(12) United States Patent
Koch et al.

(10) Patent No.: US 10,746,822 B2
(45) Date of Patent: Aug. 18, 2020

(54) SYSTEM AND METHOD FOR LOCALIZED PROCESSING OF QUANTITATIVE SUSCEPTIBILITY MAPS IN MAGNETIC RESONANCE IMAGING

(71) Applicant: THE MEDICAL COLLEGE OF WISCONSIN, INC., Milwaukee, WI (US)

(72) Inventors: Kevin Koch, Wauwatosa, WI (US); Casey Anderson, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 71 days.

(21) Appl. No.: 15/739,025

(22) PCT Filed: Jun. 22, 2016

(86) PCT No.: PCT/US2016/038723
§ 371 (c)(1),
(2) Date: Dec. 21, 2017

(87) PCT Pub. No.: WO2016/209930
PCT Pub. Date: Dec. 29, 2016

(65) Prior Publication Data
US 2018/0180688 A1  Jun. 28, 2018

Related U.S. Application Data

(60) Provisional application No. 62/183,802, filed on Jun. 24, 2015, provisional application No. 62/235,709, filed on Oct. 1, 2015.

(51) Int. Cl.
*G01R 33/24* (2006.01)
*A61B 5/055* (2006.01)
(Continued)

(52) U.S. Cl.
CPC .......... *G01R 33/243* (2013.01); *A61B 5/0042* (2013.01); *A61B 5/055* (2013.01);
(Continued)

(58) Field of Classification Search
CPC ................. G01R 33/243; G01R 33/16; G01R 33/56536; G01R 33/24; G01R 33/443;
(Continued)

(56) References Cited

U.S. PATENT DOCUMENTS 6,477,398 B1    11/2002 Mills
7,952,353 B2 *   5/2011 Lu ....................... G01R 33/243
                                                                  324/307

(Continued)

OTHER PUBLICATIONS

International Search Report and Written Opinion for International Patent Application No. PCT/US2016/038723 dated Sep. 8, 2016.

*Primary Examiner* — Dixomara Vargas
(74) *Attorney, Agent, or Firm* — Quarles & Brady LLP (57) ABSTRACT

Systems and methods for quantitative susceptibility mapping ("QSM") using magnetic resonance imaging ("MRI") and a localized processing technique are described. A field-shift map is processed based on localized regions of local field perturbations. These localized field-shift regions are processed using established QSM algorithms, or using direct dipole inversion techniques, to compute regional susceptibility distributions from the localized field shift information. When the localized regions correspond to subvolumes of the field-shift map, local susceptibility maps can be generated and combined to form a composite quantitative susceptibility map. By computing regional susceptibility distributions based on localized field-shift information, residual streaking artifacts in the susceptibility map are constrained to the individual volumes from which they originate, thereby eliminating their propagation through the image.

16 Claims, 6 Drawing Sheets

(51) Int. Cl.

| | |
|---|---|
| *G01R 33/16* | (2006.01) |
| *G01R 33/565* | (2006.01) |
| *A61B 5/00* | (2006.01) |
| *G01R 33/44* | (2006.01) |
| *G01R 33/56* | (2006.01) |
| *G01R 33/561* | (2006.01) |
| *G06T 11/00* | (2006.01) |
| *A61B 5/08* | (2006.01) |
| *A61B 5/0402* | (2006.01) |

(52) U.S. Cl.
CPC ............ *A61B 5/7285* (2013.01); *G01R 33/16* (2013.01); *G01R 33/24* (2013.01); *G01R 33/443* (2013.01); *G01R 33/5602* (2013.01); *G01R 33/5616* (2013.01); *G01R 33/56536* (2013.01); *G06T 11/008* (2013.01); *A61B 5/0402* (2013.01); *A61B 5/0816* (2013.01); *A61B 5/4082* (2013.01); *A61B 5/4088* (2013.01); *A61B 5/7257* (2013.01); *A61B 2576/026* (2013.01)

(58) Field of Classification Search
CPC ............ G01R 33/5603; G01R 33/5616; A61B 5/055; A61B 5/7258; A61B 5/7285; A61B 5/0042

See application file for complete search history.

(56) References Cited

U.S. PATENT DOCUMENTS

| | | | |
|---|---|---|---|
| 8,422,756 B2 | 4/2013 | Haacke et al. | |
| 8,781,197 B2* | 7/2014 | Wang | ............... G01R 33/54 382/131 |
| 9,513,359 B2* | 12/2016 | Koch | ............... G01R 33/56563 |
| 2011/0044524 A1* | 2/2011 | Wang | ............... G01R 33/54 382/131 |
| 2014/0062475 A1* | 3/2014 | Koch | ............... G01R 33/56563 324/309 |
| 2014/0142417 A1 | 5/2014 | Reeder et al. | |
| 2015/0145515 A1 | 5/2015 | Liu | |

* cited by examiner

SYSTEM AND METHOD FOR LOCALIZED PROCESSING OF QUANTITATIVE SUSCEPTIBILITY MAPS IN MAGNETIC RESONANCE IMAGING

CROSS-REFERENCE TO RELATED APPLICATIONS

This application represents the national stage entry of PCT International Application No. PCT/US2016/038723 filed on Jun. 22, 2016, which claims the benefit of U.S. Provisional Patent Application Ser. No. 62/183,802, filed on Jun. 24, 2015, and entitled "SYSTEM AND METHOD FOR PARCELLATED VOLUME PROCESSING OF QUANTITATIVE SUSCEPTIBILITY MAPS IN MAGNETIC RESONANCE IMAGING," and also claims the benefit of U.S. Provisional Patent Application Ser. No. 62/235,709, filed on Oct. 1, 2015, and entitled "SYSTEM AND METHOD FOR LOCALIZED PROCESSING OF QUANTITATIVE SUSCEPTIBILITY MAPS IN MAGNETIC RESONANCE IMAGING," all of which are herein incorporated by reference in their entirety.

BACKGROUND OF THE INVENTION

The field of the invention is systems and methods for magnetic resonance imaging ("MRI"). More particularly, the invention relates to systems and methods for quantitative susceptibility mapping using MRI.

When placed in an external magnetic field, such as the $B_0$ field of an MRI scanner, the magnetic susceptibility of non-ferromagnetic biomaterials generate local magnetic fields in the scanner. This susceptibility is an important physical property of tissue and has emerged as a new contrast mechanism in MRI.

Quantitative susceptibility mapping ("QSM") is an imaging technique that provides high anatomical contrast and measurements of tissue susceptibility based on biomaterial compositions. As a result, QSM can be advantageously used for monitoring iron overload in diseases such as in Alzheimer's disease; for monitoring demyelinating diseases, such as Parkinson's disease and multiple sclerosis; for monitoring calcifications in the brain and other tissues; and for performing functional MRI. Further applications include monitoring iron overload in the liver and for use in tractography with susceptibility tensor imaging.

However, the potential of QSM MRI is hindered by the inadequacy of the algorithms that are used to process imaging data, requiring long scan times and producing imaging artifacts. A challenge in QSM is that the algorithms used for generating a quantitative susceptibility map from magnetic field shift and susceptibility data are based on a mathematical relationship that is an "ill-posed" inverse problem, which produces unresolvable ambiguities in the absence of additional data. Additional information can be imposed to calculate unambiguous solutions via data from acquisitions at multiple orientations to the magnetic field. While this approach remains the gold standard for accurate susceptibility maps, it is not feasible in a clinical setting. Single-orientation datasets can impose additional constraints in the computation through numerical "regularization." This approach is, however, limited in its ability to address the challenges posed by the QSM inversion problem.

In clinically obtained datasets, images are routinely plagued by large heterogeneities and susceptibility variations. In addition, images can suffer from limited scan times and patient motion caused by discomfort. As a result, issues in the tissue masking, phase unwrapping, background field removal, and regularized field inversion algorithms used in susceptibility mapping can be significant, generating regions of large signal fluctuations and poor data consistency. As such, the resulting susceptibility maps are highly subject to streaking artifacts, which severely limits their ability for reliable analysis in the clinic. While modifications and manual processing of these datasets can reduce these issues, ideally an automated, fast, and robust technique would be applied for clinical compatibility.

The most widely applied algorithm for QSM is Morphology Enabled Dipole Inversion ("MEDI"), which exploits the structural consistency between the susceptibility map and the magnitude image reconstructed from the same gradient echo MRI. In principle, the contrast change, or "edge" on a magnitude image, arises from the underlying change of tissue type, which is the same cause for the change of magnetic susceptibility. But, images produced by MEDI still exhibit undesirable artifacts in whole-volume processing.

There are several existing methods that can mitigate streaking artifacts in QSM, but they are not without their drawbacks. As one example, thresholding algorithms can be modified to aggressively mask all field estimates at the periphery of the brain. This approach, however, erodes visualization of the brain and, in many cases, also erodes regions of good field estimates. As a consequence of this processing, susceptibility values may be lost in clinically important regions.

As another example of processing techniques for removing streaking artifacts, higher regularization penalties can be imposed in the optimization, though at a severe cost to the resolution of the resulting quantitative susceptibility map.

It would therefore be desirable to provide a method for producing quantitative susceptibility maps that overcomes the drawbacks and limitations of currently existing algorithms. In particular, it would be desirable to provide a method that reduces artifacts in the generated quantitative susceptibility maps, and that is more computationally efficient than currently existing algorithms.

SUMMARY OF THE INVENTION

The present invention overcomes the aforementioned drawbacks by providing a method for producing a quantitative susceptibility map using magnetic resonance imaging (MRI) based on localized magnetic field shift information. Magnetic resonance data acquired with an MRI system is provided for processing, and a field-shift map is generated from the magnetic resonance data. This field-shift map depicts susceptibility-induced resonance frequency shifts in a volume. A susceptibility map that depicts quantitative susceptibility values in the volume is then generated by computing a magnetic susceptibility value at each voxel location in the field-shift map. The magnetic susceptibility value at a selected voxel is computed based on field-shift map values in a region localized to and containing the selected voxel location. As one example, the magnetic susceptibility value at the selected voxel location is computed based on field-shift map values contained only in a kernel centered on the selected voxel location.

It is another aspect of the invention to provide a method for producing a quantitative susceptibility map using magnetic resonance imaging ("MRI"). Magnetic resonance data acquired with an MRI system are provided, whether the data are actively acquired or retrieved from a data storage device. A field-shift map is generated from the magnetic resonance data. This field-shift map depicts susceptibility-induced resonance frequency shifts in a volume. The field-shift map is then divided into a plurality of local field-shift maps, each corresponding to a subvolume of the volume. A local susceptibility map is generated for each subvolume by performing a quantitative susceptibility mapping ("QSM") inversion algorithm on each respective local field-shift map. A composite susceptibility map is then formed by combining the local susceptibility maps. This composite susceptibility map depicts quantitative values of susceptibility throughout the volume.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for quantitative susceptibility mapping ("QSM") using magnetic resonance imaging ("MRI"). It is a discovery of the invention that, to a very good approximation, localized magnetic field information can be exclusively relied upon to derive regional susceptibility distributions.

As one example of exploiting local field shift information to compute regional susceptibility distributions with reduced streak artifacts, a kernel-based technique is utilized. In this technique, a field shift map is processed on a kernel-by-kernel basis to compute the susceptibility value of the voxel located at the center of each kernel. The kernel is moved to each voxel in the field shift map to generate a susceptibility map for the volume depicted in the field shift map. As one example, quantitative susceptibility values can be computed at a given voxel location using a dipole source model fit to the field shift values contained in the kernel. By processing the field shift map on a voxel-by-voxel basis, the computational efficiency of the QSM algorithms can also be improved, such as by distributing the independent QSM inversion for the individual voxel locations across multiple computer processors or graphical processing units ("GPUs").

The kernel-based processing technique independently solves for a susceptibility value at each voxel, which eliminates all streaking across the resulting susceptibility map. As will be described below, this method can also be implemented to compute susceptibility values at multiple voxel locations contained within the kernel. By selecting the kernel size to be the same size as a block of voxels for which susceptibility values are to be computed, the kernel-based technique can be viewed as parcellating the field shift map into multiple different subvolumes that are individually processed.

Thus, as another example of exploiting local field shift information to compute regional susceptibility distributions with reduced streak artifacts, a volume-parcellated technique is utilized. In this technique, a field shift map is segmented into multiple subvolumes, or parcels, of local field perturbations. These parcellated field shift maps can then be processed using established QSM algorithms. Following their independent processing, the individual parcels are combined to form a composite image, or quantitative susceptibility map. Using this technique, residual streaking artifacts in the composite susceptibility map are constrained to the individual volumes from which they originate, thereby eliminating their propagation through the image. By parcellating the field shift map, the computational efficiency of the QSM algorithms can also be improved, such as by distributing the independent QSM inversion for the individual parcels across multiple computer processors. This technique can be viewed as an extension of the kernel-based approach, whereby susceptibility values are computed for each voxel in a kernel with a size corresponding to the field shift map subvolume.

Susceptibility maps generated from symptomatic subjects are more prone to streaking artifacts because these subjects tend to move during imaging and/or they present with large susceptibility variations from tumors, resections cavities, and hemorrhages. Consequently, complications when preprocessing QSM data are often difficult to avoid, resulting in regions of inaccurate frequency-offset estimates. These regions of poor field estimates are the source of streaking artifacts in conventionally applied regularized QSM methods.

One advantage of the localized QSM technique described here is the isolation of "bad" input map voxels and the resulting streak artifacts. Bad voxels are an inevitability in any robust QSM implementation; however, the localized approach described here constrains the effects of these bad voxels to localized regions, whereas existing global QSM approaches suffer streaking artifacts across the entire field-of-view from these bad source voxels.

The systems and methods described here provide advantages over existing techniques for quantitative susceptibility mapping. As one example, the systems and methods for localized QSM described here significantly reduce the quantity and severity of streaking artifacts in quantitative susceptibility maps. Regions of poor field information are inevitable in clinical datasets and result in streaking artifacts in quantitative susceptibility maps. The systems and methods for localized QSM described here, however, keep these streaking artifacts isolated to a local sub-volume, thereby increasing the quality and robustness of the generated quantitative susceptibility maps. For sub-volumes with high field information, less reliance on the regularization is needed to eliminate the streaking artifacts compared to a full volume analysis, thereby increasing the resolution and accuracy of the local susceptibility map.

The systems and methods for localized QSM described here are also capable of achieving enhanced computational performance relative to currently available QSM techniques. Although multiple kernels or volumes need to be generated when implementing the localized QSM techniques described here, parallel computation with analytic solutions can be employed to improve computational performance relative to full volume iterative solutions. As one example, the systems and methods for localized QSM described here are faster that implementations of MEDI. With reduced volumes and a higher data percentage, iterative and analytical regularization times are greatly decreased in the local analysis.

Another benefit of the systems and methods for localized QSM described here is their ability to achieve real-time QSM. Because of the efficiencies provided by the localized QSM techniques described here, optimizations can be performed in significantly less time that currently available QSM techniques, which indicates that real-time QSM is viable.

Advantageously, the systems and methods for localized QSM described here can be employed with any of the currently available algorithms used for generating quantitative susceptibility maps. It is contemplated that improved regularization techniques, such as CCD and projection on to convex sets (which eliminate artifacts globally), may further improve the quality of susceptibility maps when implemented with localized QSM.

Figure 1:
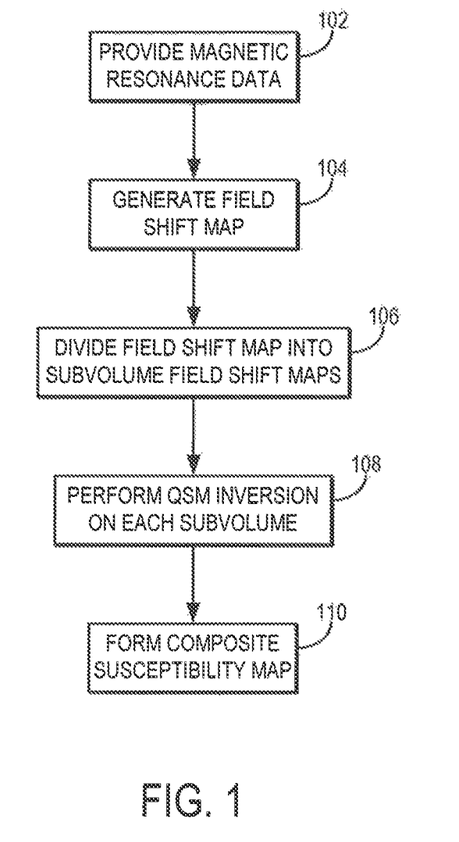
FIG. 1 is a flowchart setting forth the steps of an example method for generating a quantitative susceptibility map using localized processing of a field shift map implemented by a parcellated volume processing technique.

Referring now to FIG. 1, a flowchart is illustrated as setting forth the steps of an example method for producing a quantitative susceptibility map using parcellated volume processing to take advantage of localized field shift information for computing regional susceptibility distributions. The method includes providing magnetic resonance data to be processed, as indicated at step 102. As one example, the magnetic resonance data can be provided by retrieving previously acquired data from data storage. As another example, magnetic resonance data can be acquired with an MRI system and provided to a computer system, such as the MRI system workstation or other suitable computer system, for processing. In either case, the magnetic resonance data are suitable for generating quantitative susceptibility maps. For instance, the magnetic resonance data can include susceptibility-weighted data acquired using a suitable pulse sequence, such as a $T_2^*$-weighted pulse sequence or other pulse sequence capable of producing enhanced image contrast in areas with different susceptibility than surrounding tissue.

The provided magnetic resonance data are then processed to generate a field shift map, as indicated at step 104. The field shift map, $\delta$, indicates regions where field offsets resulting from significant differences in local magnetic susceptibility are present. The field shift map, $\delta$, is then divided, or parcellated, into a number of subvolume field shift maps, $\delta_k$, as indicated at step 106.

Figure 2:
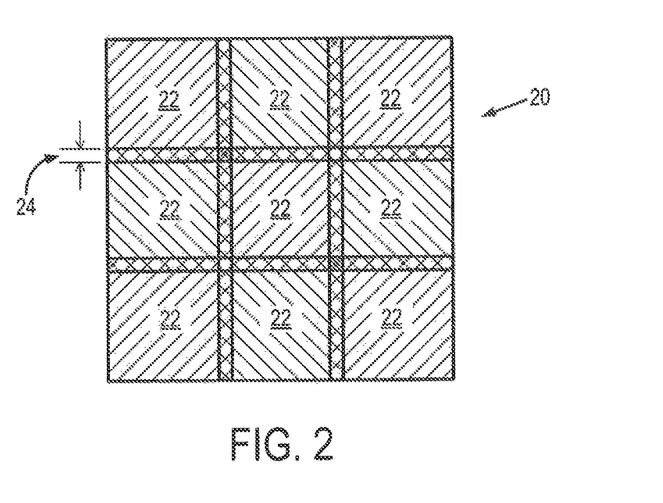
FIG. 2 illustrates an example of subdividing an acquisition or image volume into a plurality of overlapping subvolumes, or parcels.

Referring now to FIG. 2, for the parcellation of the field shift map the image volume 20 associated with the field shift map is divided into a plurality of subvolumes 22 that are each smaller than, and contained within, the original image volume 20. Preferably, these subvolumes 22 are at least partially overlapping, as indicated by overlapping regions 24. By overlapping the subvolumes 22, local field effects can be more reliably accounted for during the inversion process used to generate the quantitative susceptibility maps. As one example, the field shift map is divided into regularly-spaced and overlapping volumetric parcels.

To better understand how subdividing the acquisition volume into smaller overlapping parcels is beneficial, the effect of susceptibility sources on the boundaries of individual volumetric parcels can be considered. A voxel of susceptibility $\chi \ll 1$ can be simulated as a sphere of radius, a, that is half of the maximal voxel width. In a static magnetic field, $B_0$, this susceptibility source induces a shift, $B_{in}$, outside the voxel. This shift can be calculated as, $$B_{in}(x, y, z) = \frac{B_0 \chi a^3}{3} \frac{2z^2 - x^2 - y^2}{(x^2 + y^2 + z^2)^{5/2}}; \quad (1)$$

where x, y, and z are the distances in each principle direction from the voxel center. The maximum field perturbation at a distance, r, from a susceptibility source occurs along the principle direction of the applied magnetic field ($\hat{z}$), and is given by, $$B_{in}(z) = B_0 \frac{2}{3} \left(\frac{a}{z}\right)^3 \Delta \chi. \quad (2)$$

Using estimated maximum susceptibility values and voxel dimensions in clinical brain imaging for $\Delta \chi_{max}$ and the radius, a, respectively, the threshold distance, $z_t$, at which the field perturbation $B_{min}$ from this susceptibility source provides negligible contribution to the Larmor frequency-offset can be expressed as, $$z_t = \left(a^3 \frac{2}{3} \frac{B_0}{B_{min}} \Delta \chi_{max}\right)^{1/3}. \quad (3)$$

For a target parcel volume of interest, additional spatial-frequency information up to the threshold distance, $z_t$, is padded for each principle direction prior to solving for the local susceptibility. By including this extra spatial frequency-offset information in the QSM optimization, all local susceptibility sources with significant contribution to the frequency information within the parcel volume will be included in the net susceptibility calculation.

Thus, in some embodiments, the threshold distance, $z_t$, can be used to define the amount of overlap between adjacent parcels. Using this threshold distance to define the overlap accounts for all potential susceptibility sources affecting the frequency-offset within the target parcel.

As one example, for clinical brain imaging at 3.0 T with a conservative estimate of Larmor frequency-offset accuracy $$\left(\frac{\gamma}{2\pi} B_{min}\right)$$

of 0.1 Hz, slice thickness of 2.0 mm, and maximum anticipated susceptibility value ($\Delta \chi_{max}$) of 0.30 ppm, the threshold distance, $z_t$, is calculated to be 0.7 cm.

Referring again to FIG. 1, following parcellation of the field shift map into a plurality of reduced subvolume field shift maps, a QSM inversion algorithm is performed on each individual subvolume, as indicated at step 108. In general, any suitable QSM inversion algorithm can be implemented. Non-limiting examples of QSM inversion algorithms include those implementing Morphology Enabled Dipole Inversion ("MEDI"), truncated singular value decomposition ("TSVD"), truncated k-space division ("TKD"), iterative susceptibility-weighted imaging and mapping ("iSWIM"), compressed sensing compensated ("CSC") inversion, homogeneity-enabled incremental dipole inversion ("HEIDI"), and total variation using split Bregman ("TVSB"). The parcel maps generated in this process thus represent quantitative susceptibility maps corresponding to regions of local susceptibility, $\chi_k$, associated with the subvolumes, $V_k$.

The quantitative susceptibility maps for the different subvolumes are then combined to form a composite quantitative susceptibility map, as indicated at step 110. As one example, the individual parcel maps can be stitched together to form the composite map. The stitching procedure may include scaling the parcel maps, adjusting mutual information of the overlapping regions of the parcel maps, and adjusting the dynamic range of the parcel maps.

In one embodiment, the stitching procedure includes discarding the overlapping regions and combining the parcels to produce a composite susceptibility map exhibiting distinct boundaries between adjacent parcels. To remove this effect, a linear gradient is applied along the overlapping sections during the parcel combination process. This approach weights the value of an individual voxel based on its proximity to the target parcel volume. Combining all parcels and their weighted overlapping regions, a smoother and cleaner composite susceptibility map can be produced.

It should be appreciated by those having ordinary skill in the art, however, that any number of suitable techniques for stitching or otherwise combining the individual parcel maps can be implemented.

Figure 3:
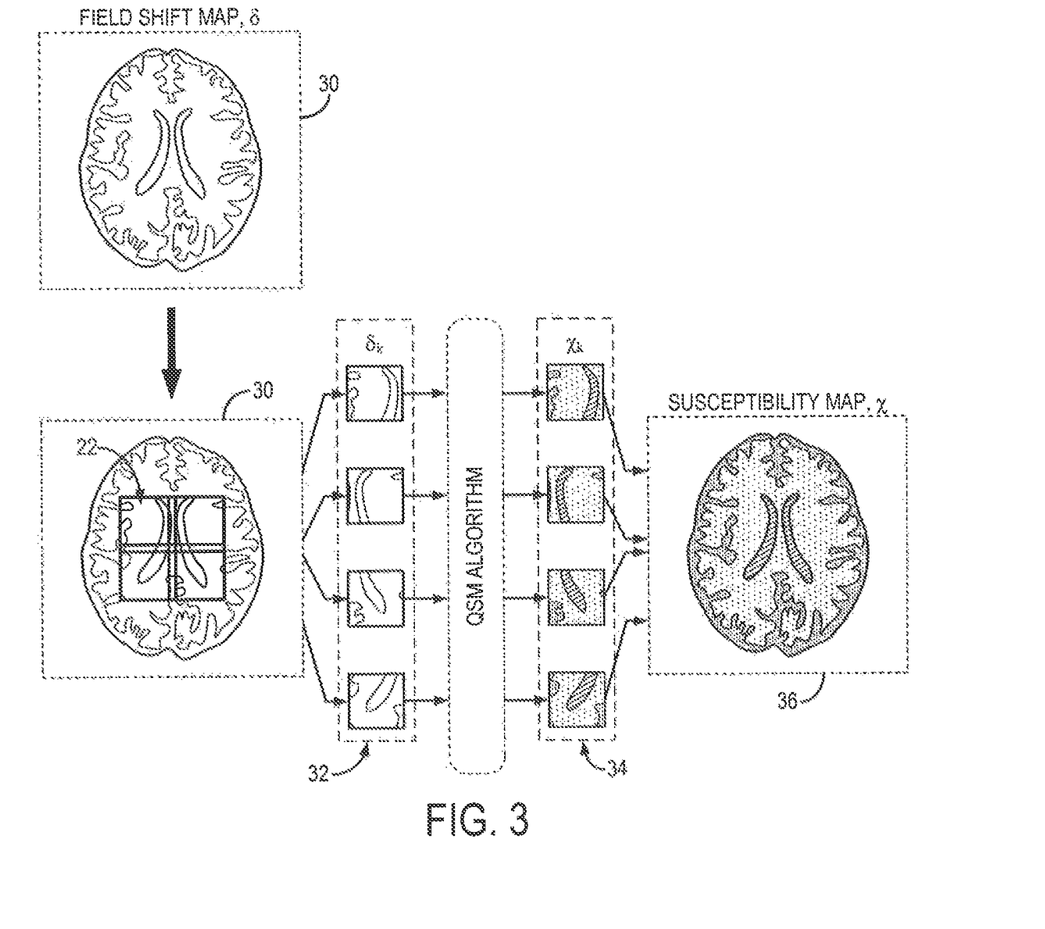
FIG. 3 is a schematic illustration of the method for generating a quantitative susceptibility map shown in FIG. 1.

The foregoing method is schematically illustrated in FIG. 3, where a field shift map 30, $\delta$, is divided into volumetric parcels 22 to create local field shift maps 32, $\delta_k$. For the sake of clarity, only four such volumetric parcels 22 are illustrated in FIG. 3; however, the entire volume is preferably divided into volumetric parcels 22. The local field shift maps 32, $\delta_k$, are then processed using any suitable QSM inversion algorithm to generate local susceptibility maps 34, $\chi_k$, associated with the volumetric parcels 22. These local susceptibility maps 34, $\chi_k$, are then stitched together, or otherwise combined, to form a susceptibility map 36, $\chi$, corresponding to the entire volume.

Figure 4:
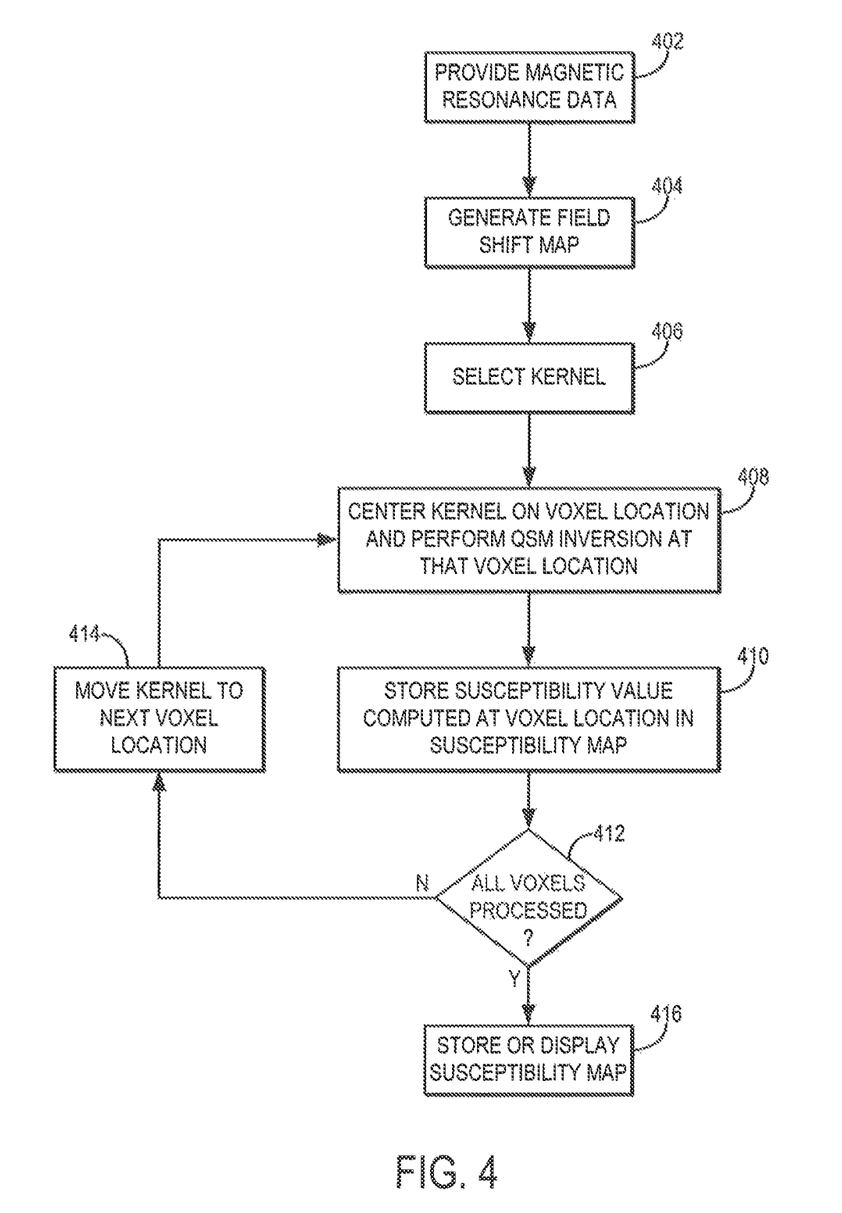
FIG. 4 is a flowchart setting forth the steps of an example method for generating a quantitative susceptibility map using localized processing of a field shift map implemented by processing voxel locations within a moving kernel.

Referring now to FIG. 4, a flowchart is illustrated as setting forth the steps of an example method for producing a quantitative susceptibility map using kernel-based processing to take advantage of localized field shift information for computing regional susceptibility distributions. The method includes providing magnetic resonance data to be processed, as indicated at step 402. As one example, the magnetic resonance data can be provided by retrieving previously acquired data from data storage. As another example, magnetic resonance data can be acquired with an MRI system and provided to a computer system, such as the MRI system workstation or other suitable computer system, for processing. In either case, the magnetic resonance data are suitable for generating quantitative susceptibility maps. For instance, the magnetic resonance data can include susceptibility-weighted data acquired using a suitable pulse sequence, such as a $T_2^*$-weighted pulse sequence or other pulse sequence capable of producing enhanced image contrast in areas with different susceptibility than surrounding tissue.

The provided magnetic resonance data are then processed to generate a field shift map, as indicated at step 404. The field shift map, $\delta$, indicates regions where field offsets resulting from significant differences in local magnetic susceptibility are present. A kernel to be used for processing the field shift map, $\delta$, is then selected, as indicated at step 406. The size of the kernel is selected to be large enough such that if a susceptibility source is located at the center of the kernel, the susceptibility source will generate a magnetic field that dissipates below a field detectability limit at the edge of the kernel. As one example, this limit is approximately 2 cm for typical QSM measurements in the human brain at 3 Tesla.

Using the selected kernel, a voxel-by-voxel QSM algorithm is implemented to compute the susceptibility values in the volume represented by the field shift map. Thus, for a given voxel in the field shift map, a QSM inversion algorithm is applied to those voxels contained within the kernel, as indicated at step 408. As one example, the susceptibility value at the selected voxel location can be computed using a dipole inversion algorithm. For instance, the susceptibility value can be computed by directly solving for the Lorentz-sphere corrected dipole "magnitude" at each subvoxel within the kernel. Over the reduced set of voxels within the kernel, the dipole inversion computation can be simplified by superimposing a set of dipole responses and simultaneously solving for the dipole amplitudes that generate the measured magnetic induction within the kernel. As another example, the susceptibility value at the selected voxel can be computed using a conventional r-space QSM method to invert the kernel; however, in general, any suitable QSM inversion algorithm can be implemented.

The susceptibility value computed at the voxel location is then stored in the corresponding voxel location in a susceptibility map, as indicated at step 410. A determination is then made at decision block 412 whether all of the voxels in the field shift map have been processed. If not, then the kernel is moved to the next voxel location, as indicated at step 414, and the susceptibility value at the next voxel location is computed as in step 408. When all of the voxels in the field shift map have been processed, the susceptibility map is stored or displayed as desired, as indicated at step 416.

Figure 5:
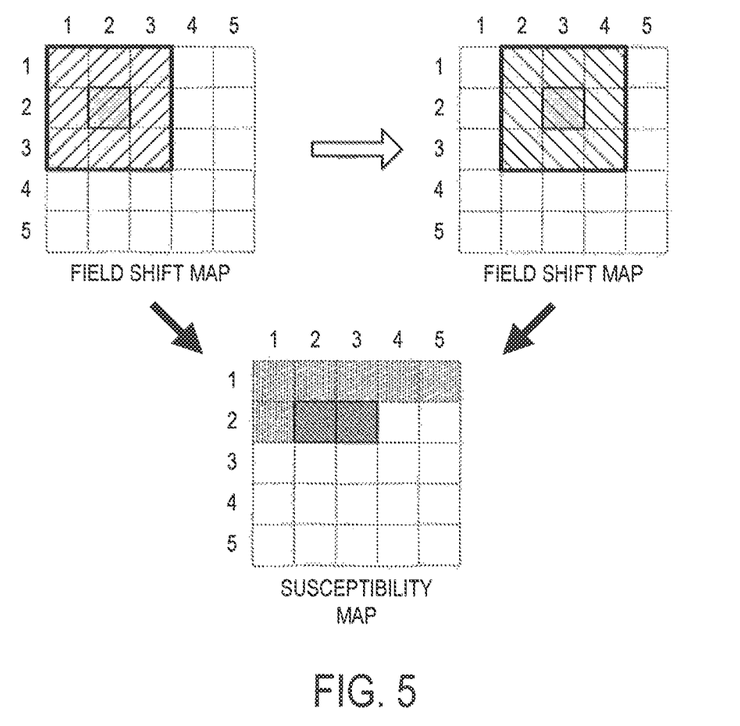
FIG. 5 is an example illustrating a kernel-based processing of two voxel locations in a field shift map.

An example of this kernel-based technique is illustrated in FIG. 5. In this example, a 3×3 kernel is first centered on a voxel at location (2,2) in the field shift map. The voxels contained within the kernel contribute to the computation of the susceptibility value at the central voxel location. The kernel is then moved to the next voxel location, (2,3), and the susceptibility value at that location is computed based on the voxels within the kernel. The result of these two steps is the computation of susceptibility values that are stored at voxel locations (2,2) and (2,3) in the susceptibility map.

Figure 6:
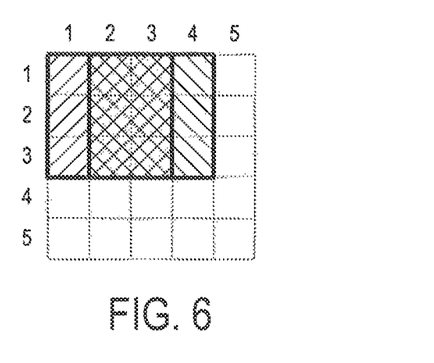
FIG. 6 illustrates an overlapping region of kernels applied to proximate voxel locations.

As shown in FIG. 6, the kernel centered at proximately located voxel locations will overlap to some degree, depending on the size of the kernel and how close the two voxel locations are to each other. The effective overlapping caused by moving the kernel from one voxel to the next in the field shift map is similar to the overlapping of subvolumes in the parcellated volume technique described above. For instance, the effective overlapping caused by moving the kernel results in local field effects being more reliably accounted for during the inversion process used to generate the quantitative susceptibility maps.

It will be appreciated by those skilled in the art that the foregoing method can be scaled to compute the susceptibility values at multiple voxel locations within a larger kernel. By selecting the kernel size to be the same as the subvolume of voxels for which susceptibility values will be computed, the foregoing method scales into the parcellated volume technique described above. As described above, the kernel-based technique independently solves for a susceptibility value at each voxel, which eliminates all streaking across transformed analysis volumes (or sub-volumes), and eliminates the need for stitching of parcels.

Thus, systems and methods have been provided that enable practical clinical utilization of quantitative susceptibility mapping through an automated, fast, and robust processing pipeline. The systems and methods described here utilize dividing the acquisition volume into multiple, preferably equally spaced and overlapping, parcels for generating local susceptibility maps that are then combined into a composite susceptibility map corresponding to the entire volume. A significant reduction in the quantity and severity of streaking artifacts can be achieved using this approach.

Regions of poor frequency-offset estimates are difficult to avoid in clinical datasets using existing QSM pre-processing methods. Using the systems and methods described here, the streaking artifacts remain isolated to a local subvolumes, thereby increasing the global quality and robustness of the generated susceptibility maps. The parcellated volume processing approach described here is also well-situated for use in distributed computing models, which can further improve the practical viability of QSM integration into clinical workflows.

Figure 7:
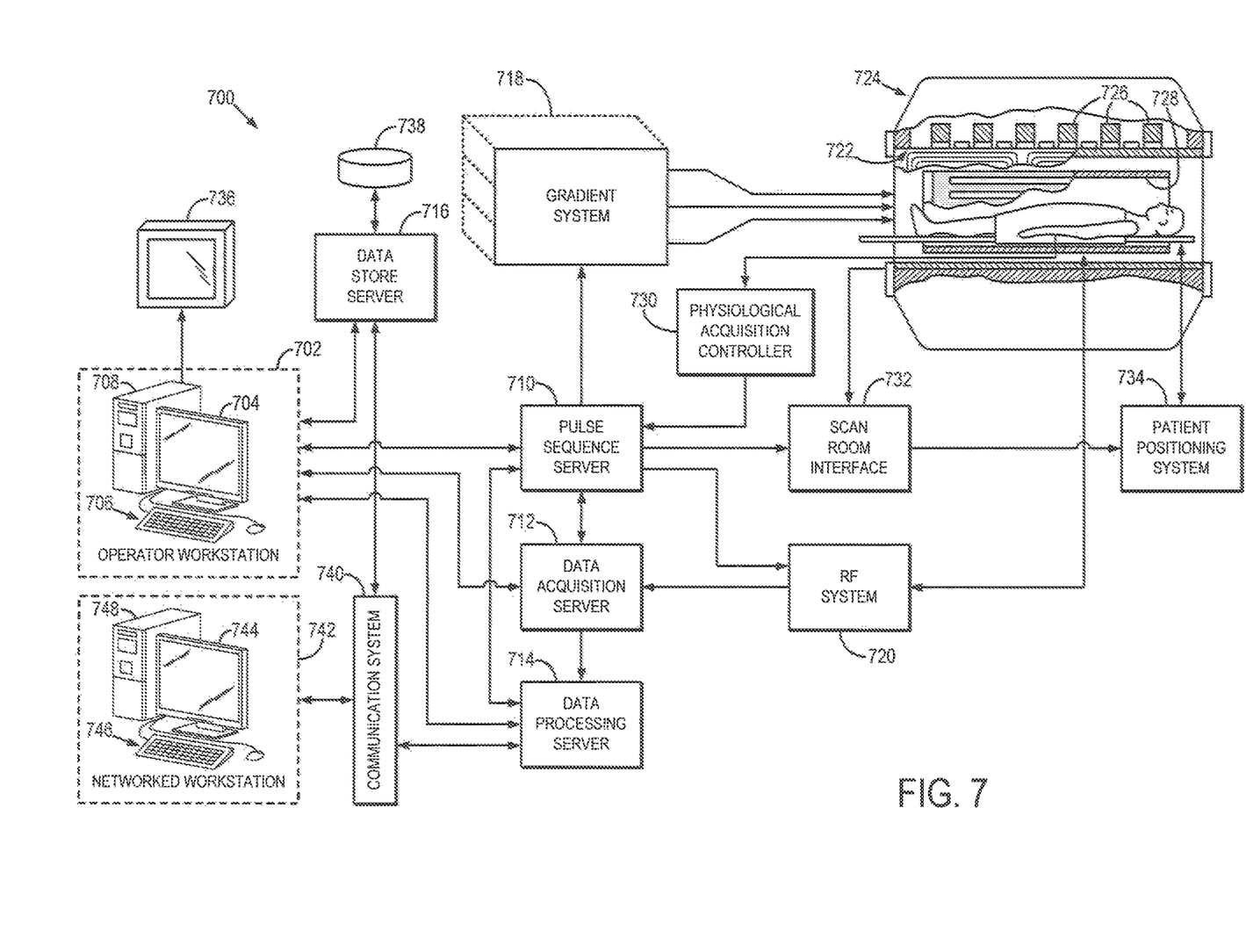
FIG. 7 is a block diagram of an example of a magnetic resonance imaging ("MRI") system.

Referring particularly now to FIG. 7, an example of a magnetic resonance imaging ("MRI") system 700 is illustrated. The MRI system 700 includes an operator workstation 702, which will typically include a display 704; one or more input devices 706, such as a keyboard and mouse; and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to four servers: a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the internet.

The pulse sequence server 710 functions in response to instructions downloaded from the operator workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil (not shown in FIG. 7), in order to perform the prescribed magnetic resonance pulse sequence. Responsive magnetic resonance signals detected by the RF coil 728, or a separate local coil (not shown in FIG. 7), are received by the RF system 720, where they are amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays (not shown in FIG. 7).

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \tag{4};$$

and the phase of the received magnetic resonance signal may also be determined according to the following relationship:

$$\varphi = \tan^{-1}\left(\frac{Q}{I}\right). \tag{5}$$

The pulse sequence server 710 also optionally receives patient data from a physiological acquisition controller 730. By way of example, the physiological acquisition controller 730 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does little more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction algorithms, such as iterative or back-projection reconstruction algorithms; applying filters to raw k-space data or to reconstructed images; generating functional magnetic resonance images; calculating motion or flow images; and so on.

Images reconstructed by the data processing server 714 are conveyed back to the operator workstation 702 where they are stored. Real-time images are stored in a data base memory cache (not shown in FIG. 7), from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744; one or more input devices 746, such as a keyboard and mouse; and a processor 748. The networked workstation 742 may be located within the same facility as the operator workstation 702, or in a different facility, such as a different healthcare institution or clinic.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

Figure 8:
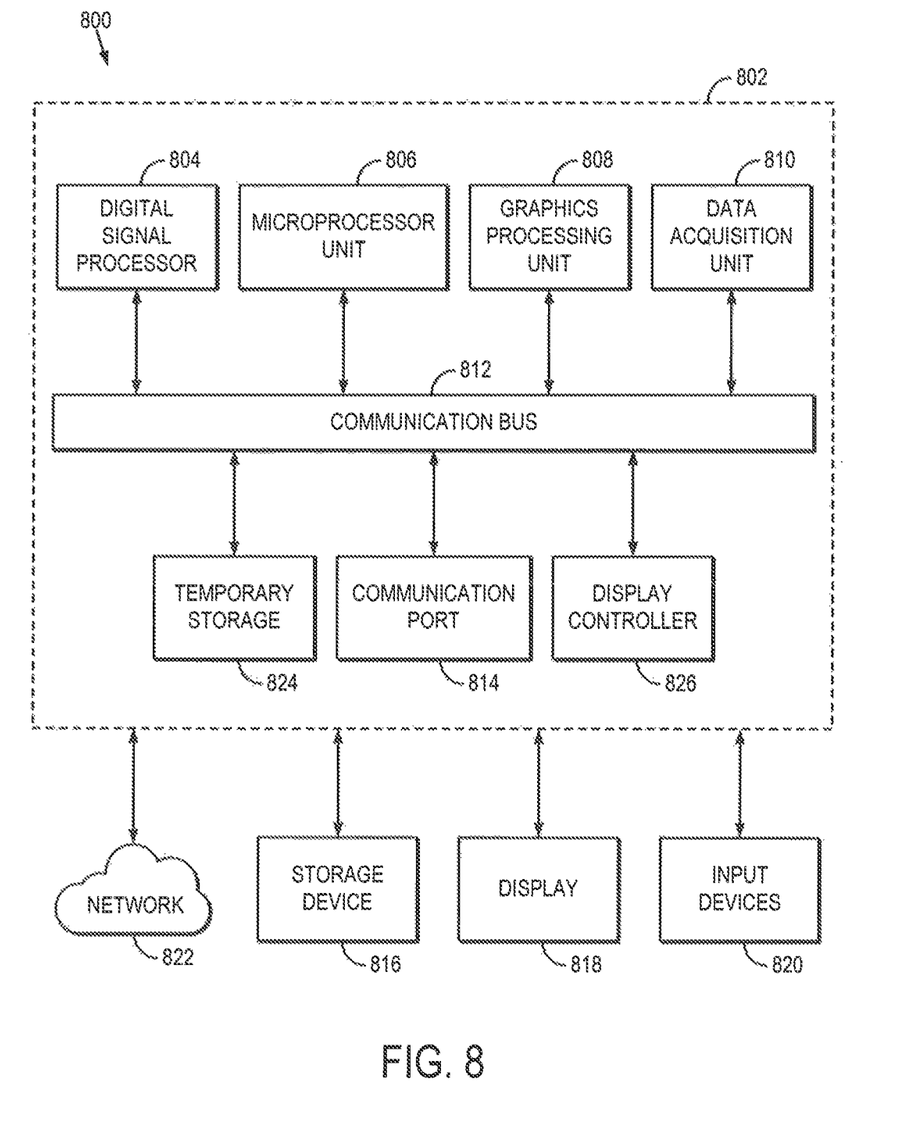
FIG. 8 is a block diagram of an example computer system that can implement the methods described here.

Referring now to FIG. 8, a block diagram of an example computer system 800 that can be configured to generate quantitative susceptibility maps using the parcellated volume techniques described here is illustrated. Magnetic resonance data or images can be provided to the computer system 800 from an MRI system, or from a data storage device, and are received in a processing unit 802.

In some embodiments, the processing unit 802 can include one or more processors. As an example, the processing unit 802 may include one or more of a digital signal processor ("DSP") 804, a microprocessor unit ("MPU") 806, and a graphics processing unit ("GPU") 808. The processing unit 802 can also include a data acquisition unit 810 that is configured to electronically receive data to be processed, which may include first and second medical images, image series, or image volumes. The DSP 804, MPU 806, GPU 808, and data acquisition unit 810 are all coupled to a communication bus 812. As an example, the communication bus 812 can be a group of wires, or a hardwire used for switching data between the peripherals or between any component in the processing unit 802.

The DSP 804 can be configured to receive and processes magnetic resonance data and magnetic resonance images. The MPU 806 and GPU 808 can also be configured to process the magnetic resonance data or magnetic resonance images in conjunction with the DSP 804. As an example, the MPU 806 can be configured to control the operation of components in the processing unit 802 and can include instructions to perform processing of the magnetic resonance data or magnetic resonance images on the DSP 804. Also as an example, the GPU 808 can process image graphics.

In some embodiments, the DSP 804 can be configured to process the magnetic resonance data or magnetic resonance images received by the processing unit 802 in accordance with the algorithms described above. Thus, the DSP 804 can be configured to generate field-shift maps; divide field-shift maps into multiple subvolumes, or volumetric parcels; implement quantitative susceptibility mapping algorithms to generate local susceptibility maps associated with the parcels; and combine local susceptibility maps into a composite susceptibility map.

The processing unit 802 preferably includes a communication port 814 in electronic communication with other devices, which may include a storage device 816, a display 818, and one or more input devices 820. Examples of an input device 820 include, but are not limited to, a keyboard, a mouse, and a touch screen through which a user can provide an input.

The storage device 816 is configured to store images, whether provided to or processed by the processing unit 802. The display 818 is used to display images, such as images that may be stored in the storage device 816, and other information. Thus, in some embodiments, the storage device 816 and the display 818 can be used for displaying magnetic resonance image, field-shift maps, and quantitative susceptibility maps, and can also be used for outputting other information, such as data plots or other reports based on the quantitative susceptibility maps.

The processing unit 802 can also be in electronic communication with a network 822 to transmit and receive data, including CT images, MR images, and other information. The communication port 814 can also be coupled to the processing unit 802 through a switched central resource, for example the communication bus 812.

The processing unit 802 can also include a temporary storage 824 and a display controller 826. As an example, the temporary storage 824 can store temporary information. For instance, the temporary storage 824 can be a random access memory.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for producing a quantitative susceptibility map using magnetic resonance imaging (MRI), the steps of the method comprising:
   (a) providing to a computer system, magnetic resonance data acquired with an MRI system;
   (b) generating a field-shift map from the magnetic resonance data using the computer system, the field-shift map depicting susceptibility-induced resonance frequency shifts in a volume;
   (c) generating with the computer system, a susceptibility map that depicts quantitative susceptibility values in the volume by computing a magnetic susceptibility value at each voxel location in the field-shift map, wherein the magnetic susceptibility value at a selected voxel is computed based on field-shift map values in a region localized to and containing the selected voxel location by:
      (i) dividing the field-shift map into a plurality of local field-shift maps, each local field-shift map corresponding to a subvolume of the volume;
      (ii) generating a local susceptibility map for each subvolume by performing a quantitative susceptibility mapping inversion algorithm on each local field-shift map; and
      (iii) forming a composite susceptibility map by combining the local susceptibility maps, the composite susceptibility map depicting quantitative values of susceptibility in the volume; and
   (d) displaying the susceptibility map with the computer system.

2. The method as recited in claim 1, wherein step (c) includes selecting a kernel and computing the susceptibility value at the selected voxel location based on field-shift map values contained in the kernel when the kernel is centered on the selected voxel location.

3. The method as recited in claim 2, wherein the susceptibility value is computed based on a dipole inversion of field shift map values contained in the kernel.

4. The method as recited in claim 1, wherein each subvolume includes at least one overlapping region in which the subvolume overlaps with an adjacent subvolume.

5. The method as recited in claim 4, wherein step (iii) includes discarding overlapping regions of the subvolumes before combining the local susceptibility maps.

6. The method as recited in claim 4, wherein step (iii) includes applying a linear gradient to overlapping regions of the subvolumes before combining the local susceptibility maps.

7. The method as recited in claim 1, wherein the subvolumes of the volume are regularly spaced.

8. The method as recited in claim 1, wherein the subvolumes of the volume at least partially overlap in an overlapping region.

9. The method as recited in claim 8, wherein the overlapping region has a size determined based on a threshold distance that accounts for including spatial frequency information from adjacent subvolumes.

10. The method as recited in claim 9, wherein the threshold distance is calculated based on a radius of a simulated susceptibility source, a main magnetic field strength of the MRI system, an estimated magnetic field perturbation associated with the simulated susceptibility source, and an estimated susceptibility value.

11. The method as recited in claim 10, wherein the radius of the simulated susceptibility source is selected as half of a maximum width of a voxel in the field-shift map.

12. The method as recited in claim 1, wherein step (iii) includes scaling the local susceptibility maps before combining the local susceptibility maps.

13. The method as recited in claim 1, wherein step (iii) includes adjusting a dynamic range of the local susceptibility maps before combining the local susceptibility maps.

14. The method as recited in claim 1, wherein step (a) includes acquiring magnetic resonance data with the MRI system.

15. The method as recited in claim 1, wherein the magnetic resonance data are magnetic resonance data that have been previously acquired by the MRI system and step (a) includes retrieving the magnetic resonance data from a data storage device.

16. A computer-implemented method for producing a quantitative susceptibility map using magnetic resonance imaging (MRI), the steps of the method comprising:
   (a) providing to a computer system, magnetic resonance data acquired with an MRI system;
   (b) generating a field-shift map from the magnetic resonance data using the computer system, the field-shift map depicting susceptibility-induced resonance frequency shifts in a volume;
   (c) dividing the field-shift map into a plurality of local field-shift maps using the computer system, each local field-shift map corresponding to a subvolume of the volume;
   (d) generating with the computer system, a local susceptibility map for each subvolume by performing a quantitative susceptibility mapping inversion algorithm on each local field-shift map;
   (e) forming a composite susceptibility map with the computer system by combining the local susceptibility maps, the composite susceptibility map depicting quantitative values of susceptibility in the volume; and
   (f) storing the composite susceptibility map in a data storage of the computer system.

* * * * *